United States Patent [19]

Oneto et al.

[11] Patent Number: 4,540,567

[45] Date of Patent: Sep. 10, 1985

[54] COSMETIC COMPOSITION

[75] Inventors: Francis E. J. Oneto, Clichy-sous-Bois; Marc Vermersch, Val d'Oise, both of France

[73] Assignee: Lever Brothers Company, New York, N.Y.

[21] Appl. No.: 76,525

[22] Filed: Sep. 17, 1979

Related U.S. Application Data

[63] Continuation of Ser. No. 842,017, Oct. 14, 1977, abandoned.

[30] Foreign Application Priority Data

Oct. 15, 1976 [GB] United Kingdom ............... 42915/76

[51] Int. Cl.$^3$ ............................................. A61K 31/22
[52] U.S. Cl. ..................................... 424/45; 424/145; 514/423; 514/548; 514/557; 514/546
[58] Field of Search ................... 424/311, 45, 145, 274

[56] References Cited

U.S. PATENT DOCUMENTS 3,535,422 10/1970 Cox et al. ............................ 424/164
3,934,028 1/1976 Lee ...................................... 424/318

FOREIGN PATENT DOCUMENTS 1388836 3/1975 United Kingdom .

OTHER PUBLICATIONS

Swanbeck, Acta Dermatovener (Stockholm) 52:406–410, (1972).
Handbook of Non-Prescription Drugs, pp. 155–160, (1973).

*Primary Examiner*—Leonard Schenkman
*Attorney, Agent, or Firm*—Milton L. Honig; James J. Farrell

[57] ABSTRACT

A cosmetically acceptable composition contains a $C_1$–$C_4$ alkyl lactate dissolved in a mixture of water and a water-miscible $C_2$–$C_4$ alkylene glycol of a polymer thereof. The composition should have stabilized pH of less than 7.

9 Claims, No Drawings

COSMETIC COMPOSITION

This is a continuation application of Ser. No. 842,017 filed Oct. 14, 1977 now abandoned.

The invention relates to cosmetically acceptable compositions for application to the skin, particularly for the prevention or treatment of acne or of other skin disorders.

The primary symptom of acne is a disorder in the keratinisation of the upper part of the pilosebacous follicle. The follicular ostium becomes obstructed by hyperkeratinised and cohesive horny cells to form a microcomedone. Due to the accumulation of these hyperkeratinised cells, the follicle develops into a microcyst which may evolve as an inflammatory lesion known as a papule, or a non-inflammatory lesion known as an open comedone. The external orifice of the follicle is not visible in the microcyst, but in the open comedone, it becomes distended by a mass of darkly pigmented horny cells.

As acne develops, the follicular epithelium may breakup and cause an eruption into the dermis of keratin and sebum. The sebum contains free fatty acids derived primarily from the lytic effect of bacterial lipases (especially from *Corynebacterium acne*) on sebum triglycerides. Inflammation due to the released free fatty acids can ensue and a lymphocyte reaction may then transform the microcyst into a papule and then into a pustule with the gathering of pus.

It is accordingly apparent that any treatment directed to inhibiting the release of free fatty acids from sebum triglycerides, and arresting hyperkeratinisation of the follicular ostium would effect a regression of the primary symptons of acne and would limit the development of new acneic lesions, particularly non-inflammatory lesions (comedones).

It has already been proposed as British Pat. No. 1 388 836 (Medisan) published Mar. 26 1975, that certain esters, such as ethyl lactate, can be employed in the form of anhydrous alcoholic solutions for the treatment of acne. According to this prior proposal, the absence of water in such compositions was considered essential in ensuring that the esters did not become prematurely hydrolysed, and hence ineffective as an acne treating material, until they had penetrated into the sebaceous glands and had dissolved in the sebum lipids. If premature hydrolysis of the esters occurred, it was apparent that skin penetration and dissolution in sebum lipids of the corresponding acid and alcohol resulting from hydrolysis would be impaired, because of their relatively low solubility compared with that of the ester. Hence, these hydrolysed esters were considered of little value in the topical treatment of acne.

Experience has subsequently shown that, although a water-free alcoholic solution of for example ethyl lactate can be topically applied to the skin, the presence of a high proportion of alcohol and the absence of water will tend to degrease and dehydrate the skin to such an extent that skin irritation and damage can occur. This was confirmed by Stotts et al in Journal of Investigative Dermatology, 69, 219 (1977), which deals with the sensitization of human skin to ethanol. It has also been confirmed that an aqueous alcoholic solution containing more than 40% by weight of ethanol is likely to cause eye irritation if applied to the face in the viscinity of the eyes. Furthermore, it is possible that excessive amounts of alcohol can stimulate sebum production which will lead to a worsening of the acneic condition.

From the foregoing, it is therefore apparent that ethanol can have a deleterious effect on the skin if applied in excessive amounts.

In attempting to avoid the occurrence of this type of problem, it was therefore necessary to devise a formulation which did not contain ethanol, or at least did not contain an excessively high proportion of ethanol, and in which ethyl lactate was both soluble and stabilised against premature hydrolysis.

It was determined that if a simple aqueous solution of ethyl lactate was employed, then hydrolysis was likely to result during storage or, when applied to the skin, before intact ethyl lactate could reach the sebum lipids in the sebaceous gland and pilosebaceous follicle.

We have now discovered that it is possible to provide an effective composition for the treatment or prevention of acne which will not dehydrate or degrease the skin and which is stabilised such that it will allow a specifically defined ester, for example ethyl lactate, to reach the sebum lipids intact following topical application of the composition.

Accordingly, one aspect of the invention is a composition which includes water, a specifically defined ester and a water-miscible solvent for that ester, the composition having a critically defined pH range.

More specifically, the invention provides a cosmetically acceptable composition for treating acne comprising a $C_1$–$C_4$ alkyl lactate, or a mixture of said lactates, dissolved in a mixture of water and a water-miscible $C_2$–$C_4$ alkylene glycol or a polymer of said glycol, which composition has a critically defined pH value of from 4 to 7, preferably from 4 to 5.5 and ideally from 4.5 to 5.0.

The invention also provides a process for effectively employing $C_1$–$C_4$ alkyl lactates as a means for treating acne comprising dissolving a $C_1$–$C_4$ alkyl lactate or a mixture of said lactates in a mixture of water and a water-miscible $C_2$–$C_4$ alkylene glycol, or a polymer of said glycol, in a manner such that the final composition has a critically defined pH value of from 4 to 7.

The invention furthermore provides a method for alleviating the symptons of acne which comprises topically applying an effective amount of a cosmetically acceptable composition to involved portions of human skin, said composition comprising from about 2% to about 50% by weight of a $C_1$–$C_4$ alkyl lactate, from about 5% to about 50% by weight of a water miscible $C_2$–$C_4$ alkylene glycol or a polymer thereof, the composition having a critically defined pH value of from 4 to 7.

The principal active compound in the composition according to the invention is one or more esters of $C_1$–$C_4$ alkyl lactates, such as, for example, ethyl lactate, n-propyl lactate, iso-propyl lactate, n-butyl lactate, iso-butyl lactate and tert-butyl lactate. Mixtures of the $C_1$–$C_4$ alkyl lactates can also be used.

The effectiveness of the foregoing class of esters is thought to be due to their ability to pass through the epidermis to reach the sebum in the sebaceous gland and pilosebaceous follicle intact, and there to dissolve in the sebum lipids where hydrolysis by lipases derived from bacterial contaminants will yield the corresponding acid and alcohol of these esters. The alcohol so formed is thought to exhibit antibacterial activity when formed in situ in the sebaceous glands and in this way the bacterial population, whose lipase activity otherwise contributes to acne formation following hydrolysis of sebum triglycerides, thus releasing free fatty acids, can thereby be reduced. Also, the lactic acid which is formed in situ is capable of reducing the pH of the environment to a value below pH 6 which will inhibit bacterial lipase activity. Free lactic acid also appears to reduce keratinisation. The net result is that release from the sebum lipids of free fatty acids (which are contributory in the development of acne) is reduced, and remission of the acne condition can be observed.

The preferred active ester is ethyl lactate.

The quantity of $C_1$–$C_4$ alkyl lactate employed in the composition forms from about 2% to about 50%, preferably from 5 to 25% by weight, based on the total weight of the composition in which it is employed. Compositions containing less than 2% by weight of the alkyl lactate are likely to be ineffective for treating acne; compositions containing more than 50% by weight of the alkyl lactate are unlikely to prove more effective in the treatment of this condition than compositions containing up to 50%.

The composition also includes a $C_2$–$C_4$ alkylene glycol, or a polymer thereof, which acts primarily as a solvent for the alkyl lactate to enable it to penetrate the skin and find its way, inter alia, into the sebaceous glands; the glycol also limits the dehydration of the skin and improves the sensory feel of the product when it is applied thereto.

The preferred $C_2$–$C_4$ alkylene glycols are n-propylene glycol, and 1,3-butylene glycol and the preferred polymers are the respective corresponding polymers polyethylene glycol having a molecular weight of up to 10,000 and polypropylene glycol having a molecular weight of up to 400.

Further examples of alkylene glycols and their corresponding polymers are ethylene glycol and its corresponding dimer and trimer.

The amount of alkylene glycol monomer or corresponding polymer employed should form from about 1% to about 80%, preferably from 15% to 40%, by weight of the total composition. Compositions containing less than 1% by weight of glycol are unlikely to limit dehydration of the skin. Conversely, compositions containing more than 80% by weight of glycol are likely to be undesirably oily in use, although still operable, but for practical considerations, should not exceed this upper limit.

It is also necessary to employ water in the composition to ensure that the skin does not become excessively dehydrated or otherwise damaged following topical application of the composition for the treatment or prevention of acne. Usually, the composition will contain from about 5% to about 50% by weight of water, preferably from 10% to 30%, based on the total weight of the composition. Use of compositions containing less than 5% by weight of water are likely to leave the skin in a partly dehydrated condition. Compositions on the other hand which contain more than 50% are likely to prove too wet for practical application to the skin, although still operable for their intended purpose.

It is indeed surprising to note that whereas the water present in the composition would be expected to induce the hydrolysis of the alkyl lactate, it has been discovered that this is not so to any marked extent, provided that a pH value within a critically defined range, preferably stabilized by a buffer, is maintained.

We have, for example, found that the percentage of ethyl lactate which had hydrolysed during storage of a composition having a pH value of less than 7 was less than 1% after nearly three weeks under ambient conditions for a composition containing 50% water. Furthermore, for a similar composition containing 25% water, the percentage of ethyl lactate which had hydrolysed, also during storage under similar conditions, was less than 1% after seven weeks.

Hydrolysis of the alkyl lactate in the composition can accordingly be substantially prevented during storage over a long period of time by the introduction of a buffer in order to maintain the pH value within the critical range of from 4 to 7, preferably from 4 to 5.5, and ideally from 4.5 to 5.0.

Suitable buffers are those which are cosmetically acceptable and soluble in the composition, and which would not otherwise detrimentally affect the function of the composition. Examples are 0.02M citric acid or 0.02M glycine adjusted to a pH value between 4 and 5.5 with triethanolamine.

Similarly, buffers can be prepared from other amino acids and from tartaric acid, maleic acid, malonic acid, and glutamic acid at a similar concentration which are adjusted to a pH value between 4 and 7 with triethanolamine or another alkanolamine organic base.

The composition according to the invention can be provided, for example, in the form of a lotion, milk, or cream, which can be applied directly to the skin, preferably by means of a pad, or a mask, tissue or towel, consisting of or impregnated with the composition. Alternatively, a mechanical applicator, such as a roll-ball dispensing device or an aerosol spray can be employed.

Depending on the nature of the composition and its intended mode of application to the skin, the composition can contain other ingredients so long as the nature and function of the composition are not detrimentally affected. Examples of other ingredients are:

Emollients, for example, stearyl alcohol, glyceryl monoricinoleate, glyceryl monostearate, sulphated tallow, propylene glycol, mink oil, cetyl alcohol, stearyl stearate, isopropyl isostearate, dimethyl brassylate, stearic acid, isobutyl palmitate, isocetyl stearate, oleyl alcohol, isopropyl laurate, hexyl laurate, decyl oleate, di-isopropyl adipate, 2-octadodecanol, iso-cetyl alcohol, myristyl ethoxymyristate, cetyl palmitate, dimethylpolysiloxane, di-isopropyl adipate, di-n-butyl sebacate, di-isopropyl sebacate, di-2-ethylhexyl sebacate, 2-ethyl hexyl palmitate, isononyl isononanoate, isodecyl isononanoate, isotridecyl isononanoate, 2-ethyl hexyl palmitate, 2-ethyl hexyl stearate, di-(2-ethyl hexyl)adipate, di-(2-ethyl hexyl)succinate, isopropyl myristate, isopropyl palmitate, isopropyl stearate, butyl stearate, glyceryl monostearate, polyethylene glycols, propylene glycol, triethylene glycol, lanolin, castor oil, acetylated lanolin alcohols, acetylated lanolin, petrolatum, isopropyl ester of lanolin fatty acids, mineral oils, butyl myristate, isostearic acid, palmitic acid, isopropyl linoleate, cetyl lactate, lauryl lactate, myristyl lactate, quaternised hydroxy alkyl aminogluconate, decyl oleate, isodecyl oleate, di-isopropyl adipate, 2-ethyl hexyl palmitate, isostearyl neo pentanoate, myristyl myristate, di-isopropyl adipate, oleyl ethoxy myristate, diglycol stearate, ethylene glycol monostearate, myristyl stearate, isopropyl lanolate;

Propellants, for example, trichlorofluoro methane, dichloro difluoromethane, dichloro tetrafluoro ethane, monochloro difluoro methane, trichlorotrifluoro ethane, propane, butane, isobutane, carbon dioxide, nitrous oxide, nitrogen (used singly or in admixture).

Solvents, in addition to the alkylene glycol, for example, ethyl alcohol, 2-ethylhexanol, ethylene carbonate, propylene carbonate, isopropanol, castor oil, linear ethoxylated polymer of methanol, ethylene glycol monoethyl ether, diethylene glycol monobutyl ether, diethylene glycol monoethyl ether, propoxylated butanol, propoxylated oleyl alcohol, butyl stearate, butyl myristate;

Humectants, for example, glycerin, sorbitol, sodium 2-pyrrolidone-5-carbonate, soluble collagen, dibutyl phthalate, gelatin, polyglycerogen, ethoxylated (10–20 moles) glucose, propoxylated (10–20 moles) glucose;

Thickeners, for example, gums, starch, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxy vinyl polymer, sodium carboxymethyl cellulose, methyl cellulose, hydroxyethyl stearate amide, ethylene glycol monostearate;

Moisturisers, for example, sodium pyrrolidone carboxylate, sodium lactate, orotic acid;

Antioxidants, for example, tocopherol, ascorbyl palmitate, propyl gallate, butylated hydroxy toluene, butylated hydroxyanisole;

Anionic emulsifiers, for example, potassium stearate, sodium stearate, ammonium stearate, triethanolamine stearate, glyceryl monostearate containing either potassium or sodium soap, sodium lauryl sulphate, sodium cetyl sulphate, glyceryl monostearate containing sodium lauryl sulphate;

Cationic emulsifiers, for example, N(stearoyl colamino formylmethyl)pyridinium chloride, N-soya-N-ethyl morpholinium ethosulphate, alkyl dimethyl benzyl ammonium chloride, di-isobutylphenoxyethoxy ethyl dimethyl benzyl ammonium chloride, cetyl pyridinium chloride;

Nonionic emulsifiers, for example, fatty acid esters of sorbitan anhydrides or ethylene oxide products of sorbitan fatty acid esters such as Span 80 or Tween 80; and pluronics which are addition products of hydropholic polyoxy ethylene groups and a hydrophilic polyoxy propylene;

Anti-inflammatory agents, for example, menthyl pyrrolidone carboxylate, glycyrrhetic acid, hydrocortizone, dexamethazone, fluocinocone acetonide and salicylate derivatives;

Healing agents, for example, zinc sulphate;

Antiseptic, antibacterial, antibiotic and/or germicidal substances to reduce inflammatory acne lesions by inhibition or elimination of skin microflora, particularly *Corynebacterium acne*, for example, chlorhexidine digluconate, cetyl trimethyl ammonium bromide and cetyl pyridinium chloride, tribromo-salicylanilide, benzalkonium chloride, dehydroacetic acid;

Keratolytic agents, for example, retinoic acid; and

Abradant agents, for example, inert particulate materials such as pumice, inorganic salts such as sodium tetraborate, decahydrate and potassium pentaborate octahydrate.

The above examples of other ingredients is not intended to be exhaustive and many others can be employed. Further examples are given in McCutcheon's "Functional Materials" 1976 Annual published by M C Publishing Co., New Jersey.

Generally, the amount of each of the above other ingredients which can optionally be employed will be that recommended by the suppliers or manufacturers or that which is conventionally employed in the art, and which will not detrimentally affect the nature and function of the composition. When an alcohol, especially ethanol, is present in the composition, it is however preferred that it does not exceed 40%, preferably 35% by weight of the composition.

It has been observed that an aqueous solution prepared simply by dissolving ethyl lactate in water hydrolyses rapidly. This accords with the teaching of the Medisan patent referred to hereinbefore. For example 90% of the ethyl lactate in a 10% by weight aqueous solution of ethyl lactate was found to be hydrolysed after a week's storage at 50° C.

In an attempt to stabilise ethyl lactate in aqueous solution during storage over a long period of time, the rate of hydrolysis of a series of 10% aqueous solutions of ethyl lactate whose pH value was stabilised at different values between 3 and 7 was studied over a period of about 8 weeks at a storage temperature of 50° C.

The pH value of each solution was maintained constant to within ±0.1 of a pH unit using a potentiostat. The quality of sodium hyroxide employed for maintaining the pH constant was a measure of the rate of hydrolysis for the samples having a pH value greater than 5. For those having a lower pH, lactic acid formed as a result of hydrolysis tended to function as a buffer. The excessive amount of sodium hydroxide added to these samples was therefore adjusted in calculating their rate of hydrolysis.

The stability of these solutions of ethyl lactate was expressed as the number of days at 50° C. necessary to hydrolyse 10% of the ethyl lactate in the solution (i.e. 1% of the ethyl lactate present in the 10% solution).

The results are set out in the following table; the results relate days of storage at 50° C. against stabilised pH.

| pH  | days storage |
| --- | --- |
| 3.0 | 1 |
| 3.5 | 1 |
| 4.0 | 2 |
| 4.5 | 40 |
| 4.7 | 50 |
| 5.0 | 22 |
| 5.5 | 10 |
| 6.0 | 8 |
| 6.5 | 2 |
| 7.0 | 1 |

It will be noted from these results that the maximum stability is obtained at a pH value of 4.7.

These results were confirmed by studying the rate of hydrolysis of ethyl lactate in aqueous solutions whose pH had been adjusted by the addition of suitable buffer prepared by mixing citric acid and triethanolamine.

The invention is further illustrated by the following examples showing typical compositions according to the invention.

These compositions can be applied to the skin using any of the devices referred to hereinbefore or can be administered by hand or finger application. Excellent results in the treatment of acne can be obtained by topical application of these compositions once or several times daily to the affected area of skin.

EXAMPLES 1-4

The following formulations represent lotions which can be used in the treatment or prevention of acne according to the invention.

|  | % w/w | | | |
|---|---|---|---|---|
|  | 1 | 2 | 3 | 4 |
| Sterilised demineralised water | 25 | 25 | 25 | 25 |
| Hydroxyethyl cellulose | 0.4 | — | 0.4 | — |
| Absolute ethanol | 25 | 25 | 25 | 25 |
| n-Propylene glycol | — | — | 38.4 | 38.4 |
| 1,3-butylene glycol | 38.4 | 38.8 | — | — |
| Para methyl benzoate | 0.2 | 0.2 | 0.2 | 0.2 |
| Ethyl lactate | 10 | 10 | 10 | 10 |
| Perfume | 1 | 1 | 1 | 1 |
|  | 100 | 100 | 100 | 100 |
| pH after 7 days' storage |  |  |  |  |
| storage at 25° C. | 6 | 6 | 5.7 | 5.7 |
| storage at 50° C. | 5.3 | 5.3 | 4.8 | 4.8 |
| Percentage of hydrolysis of ethyl lactate |  |  |  |  |
| 7 days' storage at 25° C. | 0 | 0 | 0 | 0 |
| 7 days' storage at 50° C. | 0.1 | 0.1 | 0.1 | 0.1 |

EXAMPLES 5, 6, 7 & 8

The following formulations represent lotions which can be used in the treatment or prevention of acne according to the invention.

|  | % w/w | | | |
|---|---|---|---|---|
|  | 5 | 6 | 7 | 8 |
| Water | 50 | 50 | 25 | 25 |
| Ethanol | 10 | 10 | 10 | 10 |
| n-Propylene glycol | 30 | 0 | 55 | 0 |
| 1,3-Butylene glycol | 0 | 30 | 0 | 55 |
| Ethyl lactate | 10 | 10 | 10 | 10 |
|  | 100 | 100 | 100 | 100 |

The pH value of each formulation should be adjusted to from 4 to 5.5 with the addition of 0.02M citric acid and triethanolamine.

| Percentage hydrolysis of ethyl lactate: | | | | |
|---|---|---|---|---|
| after 4.5 days storage at 50° C. | 8 | 5 | 1 | 1 |
| after 19 days storage at 25° C. | 1.6 | 1 | 0 | 0 |
| after 33 days storage at 25° C. | 8 | 1 | 1 | 1 |

Percentage hydrolysis of ethyl lactate after 53 days' storage at 25° C. was 0.9.

EXAMPLES 9, 10 & 11

The following formulation represents lotions which can be used in the treatment or prevention of acne according to the invention.

|  | % w/w | | |
|---|---|---|---|
|  | 9 | 10 | 11 |
| Hydroxyethyl cellulose | 0.15 | 0.15 | 0.15 |
| Ethyl lactate | 10.00 | 10.00 | 10.00 |
| 1-3 butylene glycol | 12.50 | 12.50 | 12.50 |
| 96% aqueous ethanol | 40.00 | 40.00 | 40.00 |
| Triethanolamine | 1.00 | 1.00 | 1.00 |
| Citric acid | 1.60 | 1.60 | 1.60 |
| Hibitane (chlorhexidine digluconate as 20% solution) | 2.50 | 2.50 | — |
| Menthyl pyrrolidone carboxylate | 1.00 | — | — |
| Glycyrrhetic acid | — | 0.50 | — |
| Zinc sulphate | — | — | 0.30 |
| Water | 30.95 | 31.45 | 34.15 |
| Perfume | 0.30 | 0.30 | 0.30 |

The pH value of each lotion should be from 4 to 5.5. Any variation outside this range can be compensated for by further addition of 0.02M citric acid or triethanolamine.

EXAMPLE 12

The following formulation represents a lotion which was used in a clinical study in the treatment of acne.

|  | % w/w |
|---|---|
| Sterilised demineralised water | 26.3 |
| Hydroxy ethyl cellulose | 0.3 |
| Absolute ethanol | 40.0 |
| Propylene glycol | 22.7 |
| Cetyl trimethyl ammonium bromide | 0.2 |
| Ethyl lactate | 10.0 |
| Perfume | 0.5 |
|  | 100.0 |

Percentage hydrolysis of ethyl lactate after 53 days' storage at 25° C. was 0.9%.

The pH value of this lotion was adjusted to about 4.7 by addition of 0.02M citric acid and triethanolamine.

Clinical Trial

Procedure

Forty five subjects aged between 13 and 29 years who had been suffering from polymorphous juvenile acne for periods ranging from 6 months to 7 years were recruited for this trial.

The ethyl lactate containing lotion and a placebo containing an ethyl lactate were applied to subjects over a period of 8 weeks.

The lotions were applied twice daily with a cotton pellet in order to cleanse the skin; no other cleansing product was used during the test period.

A count of acne lesions of all types over a skin area of 9 cm$^2$ in a severely affected site on the face or back was made by two dermatologists. For record purposes colour macrophotographs of a site generally larger than that 9 cm$^2$ site selected for counting, but including this site, were also taken.

The lesions counted were:
(a) comedones (blackheads)
(b) microcysts (including inflammatory papules)
(c) pustules (inflamed and purulent papules)
(d) nodules (large-sized inflammatory lesions).

Results

From these counts, it was possible to calculate the percentage improvement of the panel as a whole as a result of application of the ethyl lactate-containing lotion according to the invention.

The percentage improvement for each type of lesion was recorded as follows:

| (a) comedones | 59% |
|---|---|
| (b) microcysts | 79.4% |

| (c) pustules | 2% |
| (d) nodules | 0% |

It can be seen from these results that the aqueous ethyl lactate-containing lotion had a profound effect on the comedones and microcysts which represented the non-inflammatory lesions.

In a separate trial, treatment of the acne condition by the addition of an oral antibiotic substantially reduced the incident of inflammatory lesions.

It was concluded that the topical application of the aqueous ethyl lacetate lotion containing the special glycol produced a highly significant improvement in the acneic condition of the patients selected for treatment.

What is claimed is:

1. A cosmetically acceptable composition for treating acne comprising
   (a) from about 2% to about 50% by weight of a $C_1$–$C_4$ alkyl lactate;
   (b) from about 5% to about 50% by weight of water; and
   (c) from about 1% to about 80% by weight of a water-miscible $C_2$–$C_4$ alkylene glycol or a polymer thereof,
   the composition having a pH value of from 4 to 7.

2. The composition according to claim 1, wherein the alkyl lactate is ethyl lactate.

3. The composition according to claim 1, wherein the glycol is n-propylene glycol or 1,3-butylene glycol.

4. The composition according to claim 1, wherein the glycol is polyethylene glycol having a molecular weight of up to 10,000 or polypropylene glycol having a molecular weight of up to 400.

5. The composition according to claim 1, additionally comprising an effective amount of chlorhexidene digluconate to act as an antibacterial substance.

6. The composition according to claim 1, additionally comprising an effective amount of glycyrrhetic acid or menthyl pyrrolidone carboxylate to act as an anti-inflammatory substance.

7. The composition according to claim 1, additionally comprising an effective amount of zinc sulphate to act as a healing agent.

8. The composition according to claim 1, additionally comprising a propellant.

9. A method for alleviating the symptons of acne which comprises topically applying an effective amount of a cosmetically acceptable composition to involved portions of human skin, said composition comprising
   (a) from about 2% to about 50% by weight of a $C_1$–$C_4$ alkyl lactate;
   (b) from about 5% to about 50% by weight of water; and
   (c) from about 1% to about 80% by weight of a water-miscible $C_2$–$C_4$ alkylene glycol or a polymer thereof,
   the composition having a pH value of from 4 to 7.

* * * * *